(12) United States Patent
Iwase et al.

(10) Patent No.: US 9,913,948 B2
(45) Date of Patent: Mar. 13, 2018

(54) INJECTION NEEDLE ASSEMBLY AND DRUG INJECTION DEVICE

(71) Applicant: Terumo Kabushiki Kaisha, Tokyo (JP)

(72) Inventors: Yoichiro Iwase, Kanagawa (JP); Takayuki Yokota, Yamanashi (JP); Hisao Yabe, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/874,927

(22) Filed: Oct. 5, 2015

(65) Prior Publication Data

US 2016/0022924 A1    Jan. 28, 2016

Related U.S. Application Data

(63) Continuation of application No. PCT/JP2013/060429, filed on Apr. 5, 2013.

(51) Int. Cl.
*A61M 5/32* (2006.01)
*A61M 5/34* (2006.01)
*A61M 5/46* (2006.01)

(52) U.S. Cl.
CPC ........ *A61M 5/3293* (2013.01); *A61M 5/3287* (2013.01); *A61M 5/347* (2013.01); *A61M 5/46* (2013.01)

(58) Field of Classification Search
CPC ...... A61M 5/3293; A61M 5/347; A61M 5/46; A61M 5/3287
(Continued)

(56) References Cited

U.S. PATENT DOCUMENTS 4,387,879 A * 6/1983 Tauschinski ........ A61M 39/045
                                            137/846
5,342,346 A * 8/1994 Honda ................. A61J 1/2089
                                            604/411
(Continued)

FOREIGN PATENT DOCUMENTS

CN        102470220         5/2012
EP        1 452 201 A1      9/2004
(Continued)

OTHER PUBLICATIONS

International Search Report Issued in PCT/JP2013/060429 dated Jul. 9, 2013.
(Continued)

*Primary Examiner* — Manuel Mendez
(74) *Attorney, Agent, or Firm* — Foley & Lardner LLP

(57) ABSTRACT

An injection needle assembly includes an injection needle, a fitting portion, and a hub. The fitting portion is formed into a cylindrical shape and has one end serving as a fitting opening. The fitting portion includes a female taper shape in which an inner diameter of a cylindrical hole of the fitting portion becomes smaller toward an inner side. The hub includes the fitting portion for holding the injection needle. The injection needle assembly is used such that the female taper shape of the fitting portion is fitted to a drug discharge tube, which has a male taper shape in which an outer diameter of a cylinder becomes smaller toward a tip. When the male taper shape of the drug discharge tube has a taper ratio of N/100, the female taper shape of the fitting portion 12 is formed to have a taper ratio of M/100, where M>N.

17 Claims, 11 Drawing Sheets

(58) Field of Classification Search
USPC .......... 604/403, 411–413, 905; 137/799, 798
See application file for complete search history.

(56) References Cited

U.S. PATENT DOCUMENTS

| | | | |
|---|---|---|---|
| 5,360,413 A * | 11/1994 | Leason | A61M 39/26 137/843 |
| 5,374,264 A * | 12/1994 | Wadsworth, Jr. | A61J 1/1425 604/403 |
| 5,792,099 A * | 8/1998 | DeCamp | A61F 9/0017 604/117 |
| 5,964,737 A | 10/1999 | Caizza | |
| 6,511,472 B1 * | 1/2003 | Hayman | A61M 25/0097 604/533 |
| 2004/0220532 A1 | 11/2004 | Caizza | |
| 2010/0089475 A1 * | 4/2010 | Tracey | A61M 39/1011 137/799 |
| 2012/0083749 A1 | 4/2012 | Kawamoto et al. | |
| 2012/0179114 A1 | 7/2012 | Yokota et al. | |
| 2013/0079729 A1 | 3/2013 | Yokota et al. | |

FOREIGN PATENT DOCUMENTS

| | | |
|---|---|---|
| JP | 2004-329922 A | 11/2004 |
| JP | 2011-011000 A | 1/2011 |
| JP | 2011-212185 A | 10/2011 |

OTHER PUBLICATIONS

European Search Opinion and Supplementary European Search Report issued in Application No. EP 13881154.2 dated Nov. 2, 2016.

\* cited by examiner

INJECTION NEEDLE ASSEMBLY AND DRUG INJECTION DEVICE

CROSS-REFERENCE TO RELATED PATENT APPLICATION

This application is a continuation of and claims the benefit of priority from International Patent Application No. PCT/JP2013/060429, filed Apr. 5, 2013, the contents of which are incorporated herein by reference in its entirety.

TECHNICAL FIELD

The present disclosure relates to an injection needle assembly used as fitted to a drug discharge tube of an injection syringe, and a drug injection device having the injection needle assembly.

BACKGROUND

In some drug injection devices, a syringe for storing a drug for injection and an injection needle assembly having an injection needle are separately formed. After the injection needle assembly is attached to a drug discharge tube at a tip of the syringe, the drug injection device may be used to perform an injection.

The injection needle assembly is generally attached to the drug discharge tube with a taper fitting. Specifically, the drug discharge tube is formed to have a male taper shape (a shape of a circular truncated frustum of a cone) in which an outer diameter becomes continuously smaller toward a tip. On the other hand, the injection needle assembly is provided with a fitting portion having a cylindrical hole. This fitting portion is formed to have a female taper shape (a hole with a shape of a circular truncated cone) in which an inner diameter becomes continuously smaller from an opening of the cylindrical hole with a size corresponding to the drug discharge tube. The male taper shape and the female taper shape are formed with the same taper ratio. By applying pressure to the drug discharge tube and pushing the fitting portion, the tapered surfaces rub against each other and are firmly fitted to each other, whereby they are fixed to each other in a liquid-tight manner.

The taper ratio of the taper shape is expressed as a fraction, such as A/100, or as a percentage, such as A %, where, for example, a diameter decreases by A mm per 100 mm.

The International Organization for Standardization specifies taper fittings for medical equipment in ISO594-1: 1986 (Title: Conical Fittings with a 6% (Luer) Taper for Syringes, Needles and Certain Other Medical Equipment—Part 1: General Requirements) and in ISO594-2: 1998 (Title: Conical Fittings with a 6% (Luer) Taper for Syringes, Needles and Certain Other Medical Equipment—Part 2: Lock Fittings). ISO594-1 specifies a type of connection having only a taper fitting, while ISO594-2 specifies a type of connection having a taper fitting with a lock mechanism using a screw. Each standard presupposes that a taper ratio of a taper shape is 6/100.

A drug injection device fixed with a taper fitting is described in, for example, Japanese Patent Application Publication No. 2011-212185 ("Patent Literature 1"). This drug injection device is fixed using a taper fitting with a lock mechanism.

A syringe (cylindrical body) described in Patent Literature 1 has a drug discharge tube (discharge portion) with a male taper shape provided at a tip. A screw portion, serving as a lock mechanism, is provided on an outer peripheral surface of the drug discharge tube at its base. An injection needle assembly (needle hub) described in Patent Literature 1 has a cylindrical hole having a female taper shape at a fitting portion. A screw portion that threadedly engages with the screw portion of the drug discharge tube is formed on the inner peripheral surface of the fitting portion.

SUMMARY

In the drug injection device described in Patent Literature 1, the drug discharge tube of the syringe is inserted into the fitting portion of the injection needle assembly, and the syringe and the injection needle assembly are relatively rotated to allow the screw portions to be threadedly engaged with each other to attach the injection needle assembly to the syringe. The drug discharge tube is pushed into the fitting portion with the tightening action caused by the rotation, whereby the drug discharge tube and the injection needle assembly are taper-fitted to each other. By this fitting, a leakage of a drug can be prevented.

To prevent the leakage of a drug, it is necessary that the screw portions are firmly tightened to surely attain the fitting between the discharge portion and the fitting portion, and pressure is applied to cause the tapered surfaces to rub against each other. Therefore, a certain level of force is required for the tightening work. Unless the screw portions are firmly tightened, a gap is generated between the taper shapes, and a drug might leak from this gap.

When connecting a fitting portion and a drug discharge tube using only a taper fitting and without using a lock mechanism, which is different from the injection needle assembly and the drug injection device in Patent Literature 1, the injection needle assembly has to be pressed against the drug discharge tube (syringe) with a certain level of force in order to surely fix the fitting portion and the drug discharge tube to each other. If the pressing force is weak, the taper fitting is not established and a drug might leak.

As described above, a certain level of force is required to fix an injection needle assembly and a drug discharge tube and, therefore, an injection needle assembly and a drug injection device that can be surely attached to each other even with a weak force is needed.

Certain embodiments of the present invention aim to provide an injection needle assembly and a drug injection device in which a force required for an attachment between the injection needle assembly and the drug discharge tube is reduced and can be surely attached even with a weak force without causing a liquid leakage.

An injection needle assembly accomplished to attain the foregoing object includes an injection needle, a fitting portion, and a hub. The fitting portion is formed into a cylindrical shape and has one end serving as a fitting opening. The fitting portion further includes a female taper shape in which an inner diameter of a cylindrical hole of the fitting portion becomes smaller toward the inner side from the fitting opening. The hub is provided with the fitting portion for holding the injection needle. The injection needle assembly is used in such a manner that the female taper shape of the fitting portion is fitted to a drug discharge tube, which has a male taper shape in which an outer diameter of a cylinder becomes smaller toward a tip from the fitting opening. When the male taper shape of the drug discharge tube has a taper ratio of N/100, the female taper shape of the fitting portion is formed to have a taper ratio of M/100, wherein M>N.

In the injection needle assembly, the fitting portion may be formed such that M is determined based on N=6.

In the injection needle assembly, the fitting portion may be formed within a range of M=1.5 N to 10 N.

In the injection needle assembly, the fitting portion may include a guide wall that is formed on an inner wall of the cylinder hole at the fitting opening by increasing the inner diameter of the cylinder hole.

In the injection needle assembly, the drug discharge tube may include a lock mechanism provided with a screw portion, and the fitting portion may include a screw portion threadedly engaged with the screw portion of the lock mechanism.

A drug injection device according to certain embodiments of the present invention includes a syringe having the drug discharge tube and the injection needle assembly.

In the injection needle assembly and the drug injection device according to certain embodiments of the present invention, the taper ratio of the female taper shape of the injection needle assembly is larger than the taper ratio of the male taper shape of the drug discharge tube. With this configuration, the narrow outer edge of the tip of the drug discharge tube abuts the female taper shape of the injection needle assembly, whereby friction resistance is reduced, and pressure is concentrated. Therefore, the outer periphery of the tip of the drug discharge tube and the female taper shape are brought into close contact with and fitted to each other even with a weak force is used when inserting the drug discharge tube. With this, a liquid leakage can be surely prevented.

When the fitting portion is formed such that M is determined based on N=6, a syringe with a general shape according to the international standard can be used.

When the fitting portion is formed within the range of M=1.5 N to 10 N, a more surely fitting can be attained more surely, whereby a liquid leakage can be prevented more surely.

When the fitting portion has a guide wall formed on an inner wall of the cylinder hole at the fitting opening by increasing the inner diameter of the cylinder hole, an insertion opening is increased such that the drug discharge tube can easily be inserted into the injection needle assembly.

When the drug discharge tube has a lock mechanism provided with a screw portion, and the fitting portion has a screw portion that may be threadedly engaged with the screw portion of the lock mechanism, the injection needle assembly can be fixed to the drug discharge tube by pressing the injection needle assembly against the drug discharge tube. Therefore, a leakage of a drug can be surely prevented, and the holding force of the injection needle assembly attached to the drug discharge tube can be increased.

DETAILED DESCRIPTION OF THE EMBODIMENTS

While certain embodiments for carrying out the present invention will be described below in detail, the scope of the present invention is not limited to the embodiments described below.

Figure 1:
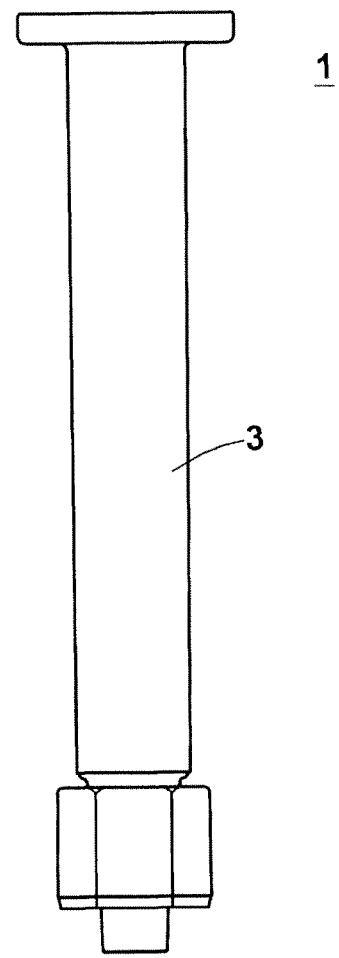
FIG. 1 is an exploded side view illustrating an injection needle assembly and a drug injection device according to a first embodiment of the present invention.
Figure 1:
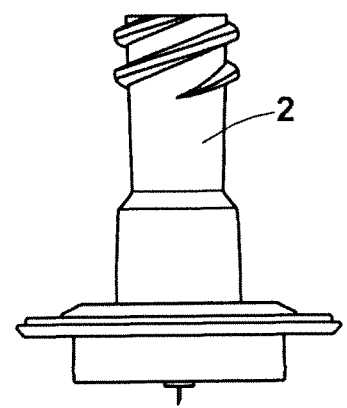

FIG. 1 is an exploded side view illustrating a first embodiment of a drug injection device 1 of the present invention. The drug injection device 1 is used for injecting a drug by puncturing a skin surface with a needle tip. Here, the drug injection device 1 for intradermal injection of a drug into an upper layer of a skin is illustrated as one example. The drug injection device 1 includes an injection needle assembly 2, and a syringe 3 to which the injection needle assembly 2 is detachably mounted. Although not illustrated, a pusher for pushing the drug is inserted into the syringe 3.

Figure 2:
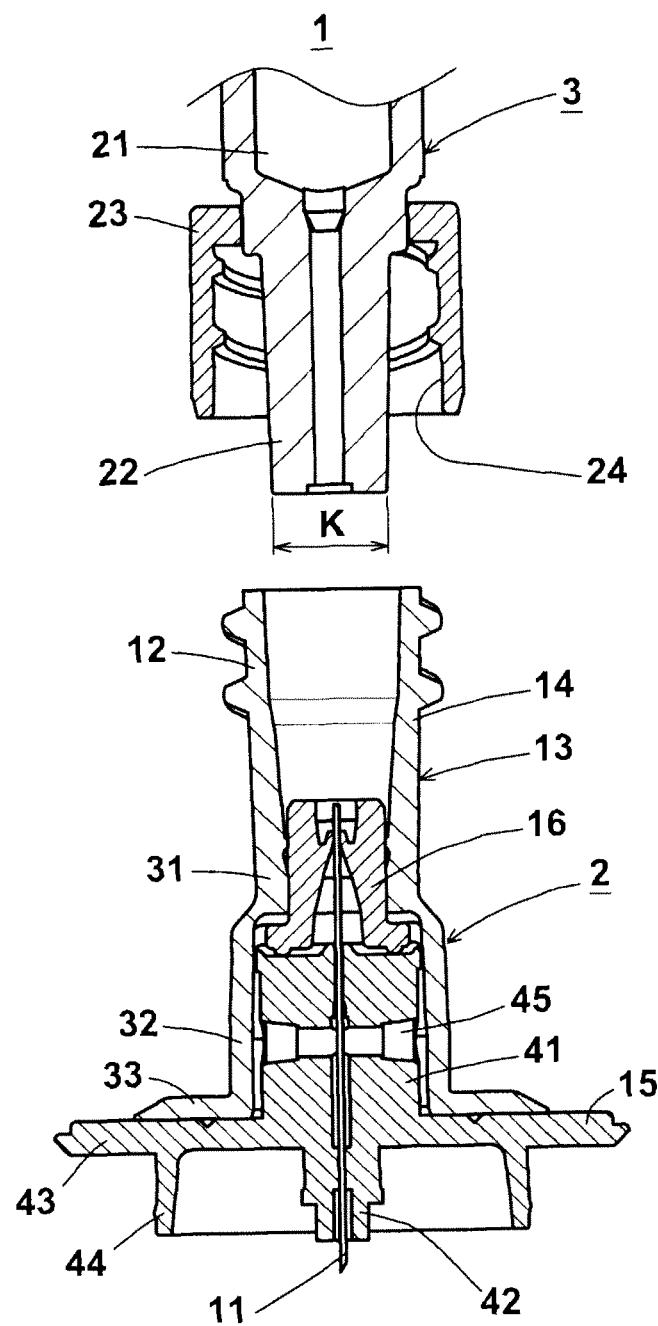
FIG. 2 is a partially enlarged sectional view illustrating the injection needle assembly and the drug injection device of the first embodiment.

FIG. 2 is a partially enlarged sectional view illustrating the drug injection device 1 illustrated in FIG. 1. FIG. 2 illustrates a tip part of the syringe 3.

The syringe 3 to which the injection needle assembly 2 is attached is, for example, a synthetic resin syringe used for a known drug injection device. The syringe 3 is made into a cylinder, and the inside of the cylinder is defined as a drug storage unit 21 that stores a drug. A cylindrical drug discharge tube 22 communicating with the drug storage unit 21 is mounted at the tip of the syringe 3.

The drug discharge tube 22 has a male taper shape in which the outer diameter of the cylinder decreases toward the tip. This taper shape is formed with a taper ratio of N/100. N is a positive number. In this example, the male taper shape is formed with N=6, which is called a luer taper, according to the standard of ISO594-1 or ISO594-2.

A flat surface orthogonal to the axial direction is formed on the tip of the drug discharge tube 22. A hole for discharging a drug is formed on the central part of the axis of the flat surface. The outer shape of the flat surface, i.e., the outer edge of the tip of the drug discharge tube 22, is a circle. The flat surface at the tip and the side face (tapered surface) of the drug discharge tube 22 communicate with each other at the outer edge of the tip of the drug discharge tube 22.

The drug discharge tube 22 has, for example, a cylindrical lock mechanism 23 provided at its back end (upper side in the figure) for coaxially surrounding the drug discharge tube 22. The cross-section of the cylinder of the lock mechanism 23 on its inner periphery is a circle, while the cross-section on its outer periphery is a hexagon by which the lock mechanism 23 is easily twisted, for example, with hands. The lock mechanism 23 is made of a member different from the syringe 3, and is fixed to the back end of the drug discharge tube 22 by bonding or fitting, or with a screw. The lock mechanism 23 has a screw portion 24 on an inner wall of the cylinder. This screw portion 24 is formed to be capable of being threadedly engaged with a screw portion 17 formed on a later-described fitting portion 12 of the injection needle assembly 2. In this example, the screw portion 24 is a female screw formed with a double helical thread groove.

The syringe 3 and the lock mechanism 23 are made of synthetic resin (plastic), for example. Examples of synthetic resin material include polypropylene, polycarbonate, polyethylene, and cycloolefin polymer.

The injection needle assembly 2 illustrated in FIG. 2 includes an injection needle 11 and a hub 13, which holds the injection needle 11 and is provided with the fitting portion 12.

The injection needle 11 is a metallic needle tube having a hollow needle hole in an axis direction. A blade surface that is to puncture a skin is formed on the tip of the injection needle 11. Known injection needles may be used as the injection needle 11. For example, a stainless steel needle with a size of 33 to 26 G (outer diameter of 0.2 to 0.45 mm) as specified in the standard (ISO 9626: 1991/Amd. 1:2001 (E)) for medical needle tubes in ISO can be used for the injection needle 11. However, it is not limited thereto.

The hub 13 may include, for example, a first member 14, a second member 15, and an elastic member 16.

The first member 14 is entirely formed into a substantially cylindrical shape. The first member 14 has the fitting portion 12, to which the drug discharge tube 22 is fitted, at one end (upper side in the figure), an intermediate portion 31, into which the elastic member 16 is inserted at a hollow central part, an insertion portion 32, into which the second member 15 is inserted on the other end, and a flange-type fixing portion 33 at an outer periphery of the other end for bonding and fixing the second member 15.

Figure 3:
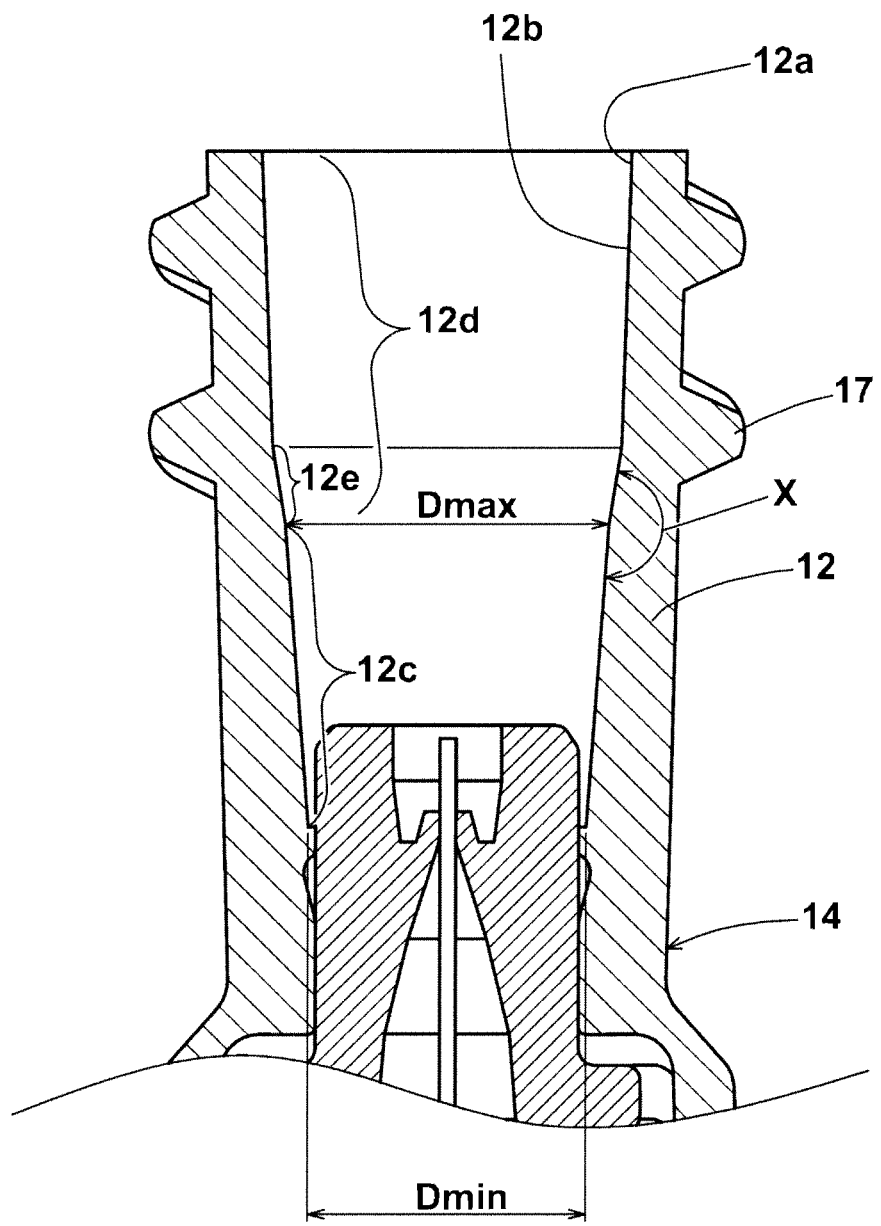
FIG. 3 is a partially enlarged sectional view illustrating the injection needle assembly of the first embodiment.

FIG. 3 illustrates an enlarged sectional view of the fitting portion 12 of the first member 14.

The fitting portion 12 is formed into a cylinder, and an opening end at its one end is specified as a fitting opening 12a to which the drug discharge tube 22 is fitted. The fitting portion 12 has a fitted wall 12c, which is fitted to the drug discharge tube 22, on the inner wall of a cylinder hole 12b. As illustrated in FIG. 3, the fitting portion 12 preferably has a guide wall 12d on the inner wall of the cylinder hole 12b at the side of the fitting opening 12a.

The fitted wall 12c is formed into a female taper shape in which the inner diameter of the cylinder hole 12b continuously decreases toward the inner side from the fitting opening 12a. This taper shape is formed with a taper ratio of M/100 where M>N. M is a positive number. In this example, M is larger than 6 based on N=6.

The fitted wall 12c is formed such that the inner diameter of the cylinder hole 12b can be fitted to the drug discharge tube 22 of the syringe 3. The cylinder hole 12b at the fitted wall 12c is formed to satisfy the relationship of Dmax>K>Dmin, where K is the diameter of the tip of the drug discharge tube 22 (see FIG. 2), Dmax is the diameter (maximum diameter) of the fitted wall 12c at the side of the fitting opening 12a, and Dmin is the diameter (smallest diameter) at the inner side. The drug discharge tube 22 is fitted such that the tip thereof is located at a position slightly inner from the position where the diameter of the cylinder hole 12b becomes K.

The guide wall 12d is formed by increasing the inner diameter of the cylinder hole 12b at the side of the fitting opening 12a. It is more preferable to form the guide wall 12d by increasing the inner diameter of the cylinder hole 12b at the side of the fitting opening 12a than that of the entire cylinder hole 12b formed from the fitted wall 12c having the taper ratio of M/100. The guide wall 12d is preferably formed to have a taper shape in which the inner diameter of the cylinder hole 12b decreases from the fitting opening 12a to the inner side.

When the length of the fitted wall 12c in the axial direction is defined as L, the length of the guide wall 12d in the axial direction is about 0.5 L to 2 L, for example.

To prevent leakage of drug solution caused by damage of the tip of the drug discharge tube 22, the guide wall 12d and the fitted wall 12c are smoothly connected to each other, so as not to form a step between the guide wall 12d and the fitted wall 12c, with a tapered connection wall 12e in which the diameter at the inner side decreases as illustrated in FIG. 3, or with a connection wall using curved lines. The angle X between the connection wall 12e and the fitted wall 12c is preferably formed to be an obtuse angle ($90°<X<180°$), more preferably formed to be $120°≤X<180°$.

The fitting portion 12 has the screw portion 17, which can threadedly engage with the screw portion 24 of the lock mechanism 23 provided to the drug discharge tube 22, on the cylindrical outer periphery, for example. In this example, the screw portion 17 is a male screw formed with a double helical screw thread. The screw portions 17 and 24 may be a single helical screw.

The second member 15 illustrated in FIG. 2 includes a columnar base portion 41 that is inserted into the insertion portion 32 of the first member 14, a columnar adjustment portion 42 that is coaxial with the base portion 41 and projects to the needle tip, a guide portion 43 formed into a flange shape at an outer periphery of the other end of the base portion 41, and a cylindrical stabilization portion 44 projecting toward the other end of the guide portion 43 so as to surround the adjustment portion 42. The base portion 41 and the adjustment portion 42 are provided with a through-hole penetrating the axis for fixing the injection needle 11.

The base portion 41 is provided with a transverse hole 45 penetrating through a side wall at the center of the side wall. The transverse hole 45 is formed for fixing the injection needle 11 with an adhesive agent inserted into the transverse hole 45. The tip end surface of the adjustment portion 42 contacts a skin, whereby the adjustment portion 42 regulates the depth of the injection needle 11 punctured into the skin. The guide portion 43 is provided for bonding and fixing the fixing portion 33 of the first member 14. The stabilization portion 44 is provided to protect the injection needle 11 in use. A cap (not illustrated) for covering the tip of the injection needle 11 is mounted to the guide portion 43 or the stabilization portion 44 when the injection needle assembly 2 is not used.

The first member 14 and the second member 15 are made of a synthetic resin with casting. Examples of a synthetic resin material include polypropylene, polycarbonate, polyethylene, and cycloolefin polymer. The first member 14 is made of a material with a hardness equal to the hardness of the material of the drug solution discharge tube 22 or made of a material softer than the drug solution discharge tube 22.

The distal end of the injection needle 11 penetrates the elastic member 16 in a liquid-tight manner. The elastic member 16 is provided to prevent leakage of a drug toward the needle tip.

The injection needle assembly 2 is manufactured as described below. First, the injection needle 11 is inserted into the through-hole of the base portion 41 of the second member 15. The needle tip of the injection needle 11 is set to project from the adjustment portion 42 by a prescribed length to be punctured into a skin and, in this state, an adhesive agent is inserted into the transverse hole 45 formed on the base portion 41 to bond and fix the second member 15 and the injection needle 11. The adhesive agent is not illustrated in the figures. Then, the elastic member 16 is inserted into the intermediate portion 31 of the first member 14. Subsequently, an adhesive agent is applied to the guide portion 43 of the second member 15, and then, the base portion 41 of the second member 15 is inserted into the insertion portion 32 of the first member 14. Then, the fixing portion 33 of the first member 14 and the guide portion 43 of the second member 15 are bonded and fixed to each other. Thus, the injection needle assembly 2 is completed.

Next, a method of attaching the injection needle assembly 2 to the drug discharge tube 22 to assemble the drug injection device 1 will be described.

FIGS. 4 to 7 illustrate states in which the drug injection device 1 is assembled by fitting the injection needle assembly 2 and the drug discharge tube 22 of the syringe 3 to each other.

Figure 4:
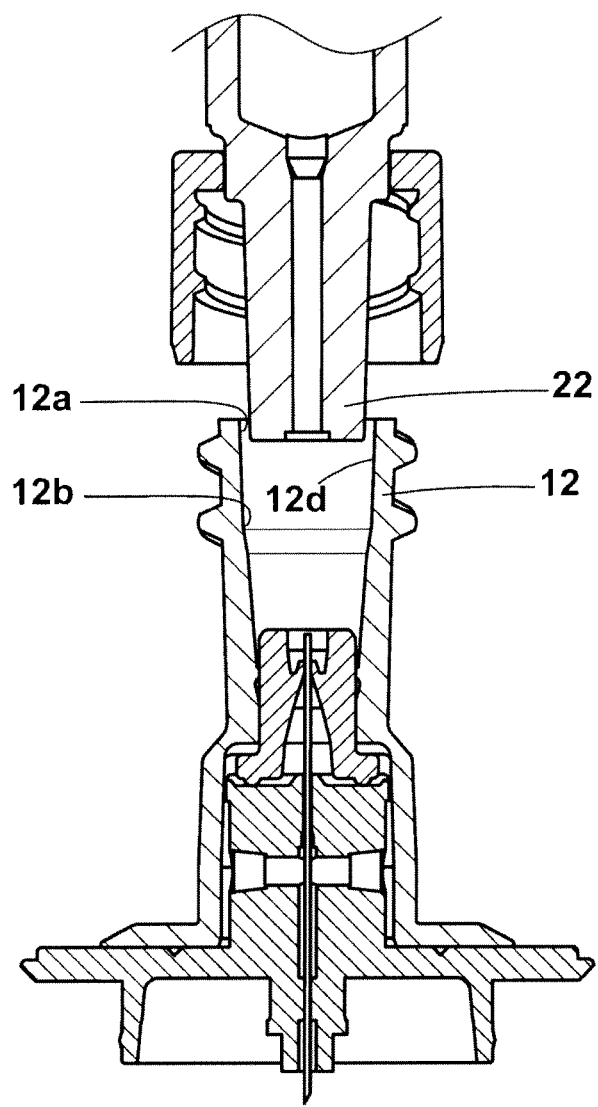
FIG. 4 is a partially enlarged sectional view illustrating a state during an assembly of the drug injection device of the first embodiment.

As illustrated in FIG. 4, the tip of the drug discharge tube 22 is inserted into the cylindrical hole 12b from the fitting opening 12a of the fitting portion 12. In this case, the tip of the drug discharge tube 22 is easily inserted into the fitting opening 12a, because the inner diameter of the guide wall 12d is formed to be large.

Figure 5:
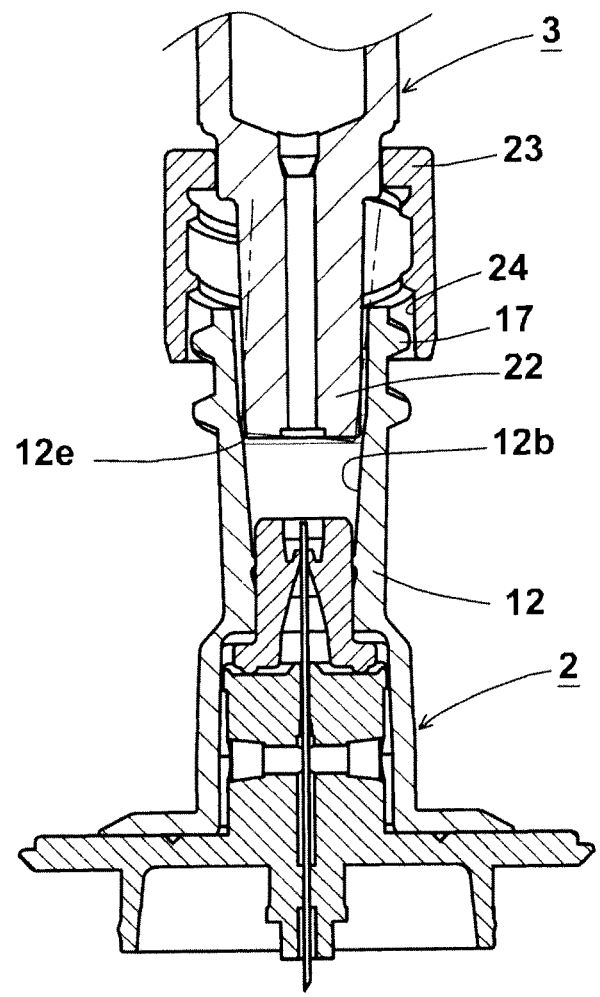
FIG. 5 is a partially enlarged sectional view illustrating a state during the assembly of the drug injection device of the first embodiment.

As illustrated in FIG. 5, the drug discharge tube 22 is further inserted into the cylindrical hole 12b. In this case, even if the drug discharge tube 22 tilts so that the tip of the drug discharge tube 22 is brought into contact with the connection wall 12e, as indicated by the two-dot-chain line in FIG. 5, the tip of the drug discharge tube 22 is not damaged because the connection wall 12e is obliquely formed into the tapered shape.

After the drug discharge tube 22 is inserted into the cylindrical hole 12b up to the position where the screw portion 24 of the lock mechanism 23 abuts the screw portion 17 of the fitting portion 12, the injection needle assembly 2 and the lock mechanism 23 (syringe 3) are relatively rotated to allow the screw portions 17 and 24 to threadedly engage with each other. The drug discharge tube 22 is deeply inserted into the cylindrical hole 12b with tightening of the lock mechanism 23.

Figure 6:
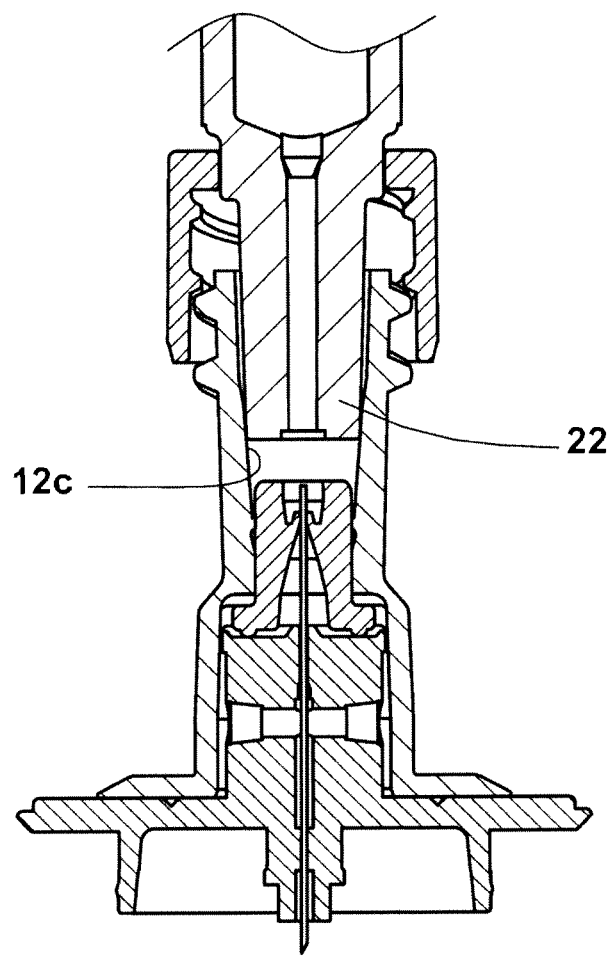
FIG. 6 is a partially enlarged sectional view illustrating a state during the assembly of the drug injection device of the first embodiment.

As illustrated in FIG. 6, the drug discharge tube 22 is brought into contact with the fitted wall 12c of the fitting portion 12 with this insertion. The taper ratio of the fitted wall 12c is larger than the taper ratio of the drug discharge tube 22. Therefore, only the outer edge of the tip of the drug discharge tube 22 is in contact with the fitted wall 12c.

Figure 7:
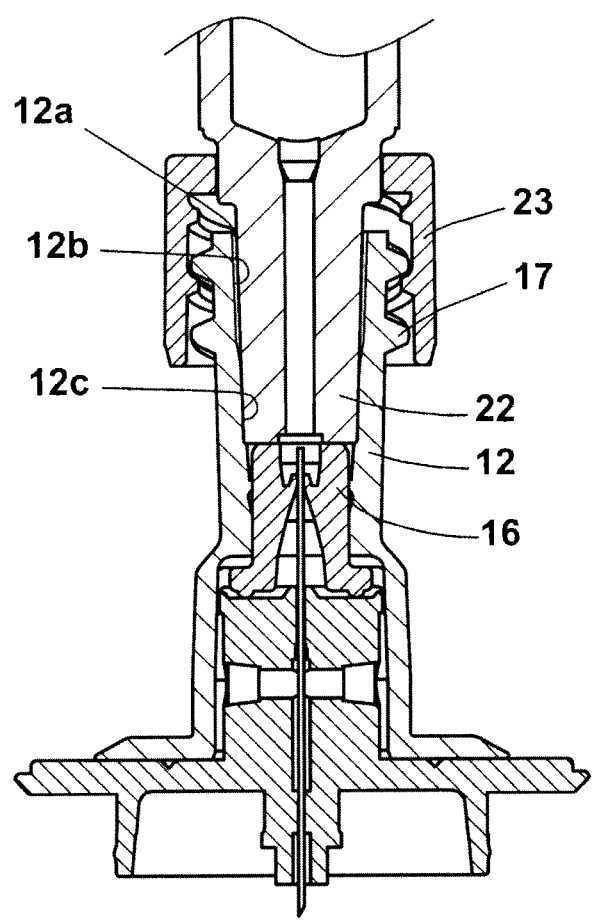
FIG. 7 is a partially enlarged sectional view illustrating a completed state of the drug injection device of the first embodiment.

As illustrated in FIG. 7, when the lock mechanism 23 is further tightened, the drug discharge tube 22 is still further inserted while the outer edge of the tip of the drug discharge tube 22 is pressed against the fitted wall 12c. With this insertion, the fitted wall 12c, made of synthetic resin, is deformed to be hollowed such that the outer edge of the tip of the drug discharge tube 22 bites into the fitted wall 12c. This allows the outer edge of the tip of the drug discharge tube 22 and the fitted wall 12c to be in close contact with each other, whereby the drug discharge tube 22 and the fitted wall 12c are fixed to each other in a liquid-tight manner. The attachment of the injection needle assembly 2 to the drug discharge tube 22 is completed in the state shown in FIG. 7, and thus, the drug injection device 1 is completed. With this state, the tip end surface of the drug discharge tube 22 and the elastic member 16 are in close contact with each other.

The outer edge of the tip of the drug discharge tube 22 is a narrow circular region. The pressure for pressing the drug discharge tube 22 against the fitted wall 12c is concentrated on this narrow region. Therefore, even if the force for pressing the drug discharge tube 22 against the injection needle assembly 2 is weak, the outer edge of the tip of the drug discharge tube 22 easily bites into the fitted wall 12c because the fitted wall 12c is easily deformed. Accordingly, the injection needle assembly 2 and the drug discharge tube 22 are firmly fitted to each other in a liquid-tight manner, whereby a liquid leakage can be surely prevented. In the conventional injection needle assembly and the drug injection device, the injection needle assembly and the drug discharge tube have a taper shape with the same taper ratio. Therefore, it is necessary to apply pressure to cause both surfaces to rub against each other, and hence, friction resistance becomes large and a relatively large force is required. However, with the drug injection device according to some embodiments of the present invention, the injection needle assembly and the drug discharge tube can be surely fitted to each other even with a weak force.

The material of the first member 14 is not limited to a relatively soft material, such as polypropylene. A relatively hard material, such as polycarbonate or cycloolefin polymer, may also be used because the drug solution discharge tube 22 sufficiently bites into the fitted wall 12c due to the pressure concentrated on the outer edge of the tip of the drug solution discharge tube 22.

A value of M in the taper ratio of the fitted wall 12c may assume any value larger than N. However, if the value of M is almost equal to N, the biting amount of the outer edge of the tip of the drug discharge tube 22 into the fitted wall 12c becomes small. Therefore, it is preferable to set M≥1.5 N (in the case of N=6, M≥9), and more preferable to set M≥2 N (in the case of N=6, M≥12). When the value of M is too much larger than N, the diameter of the cylinder hole 12b increases. Considering the realistic range of the relationship between the wall thickness and the outer diameter of the fitting portion 12, M≤10 N (in the case of N=6, M≤60) is preferable, M≤5 N (in the case of N=6, M≤30) is more preferable, and M≤3 N (in the case of N=6, M≤18) is still more preferable. For example, the range of the value of M is preferably M=1.5 N to 10 N (in the case of N=6, M=9 to 60), more preferably M=2 N to 5 N (in the case of N=6, M=12 to 30), and still more preferably M=2 N to 3 N (in the case of N=6, M=12 to 18).

Although it depends on the material of the fitting portion 12, when the lock mechanism 23 of the syringe 3 has a cylindrical shape surrounding the fitting portion 12 as illustrated in FIG. 7, the lock mechanism 23 can prevent the increase in the diameter of the cylinder hole 12b due to the deformation of the cylinder hole 12b caused by the pressure upon fitting the drug discharge tube 22. Accordingly, the drug discharge tube 22 and the fitted wall 12c can be more surely fitted to each other. It is preferable that the screw portion 17 is formed on the outer periphery close to the fitting opening 12a of the fitting portion 12 such that the lock mechanism 23 surrounds the portion near the fitting opening 12a of the fitting portion 12 having a small thickness.

Figure 8:
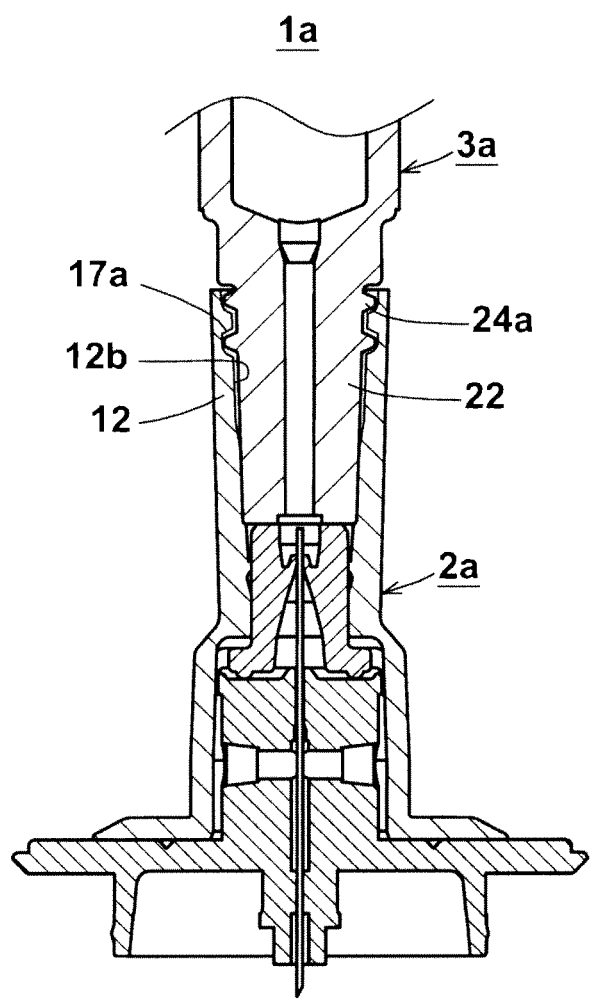
FIG. 8 is a partially enlarged sectional view illustrating an injection needle assembly and a drug injection device according to a second embodiment of the present invention.
Figure 9:
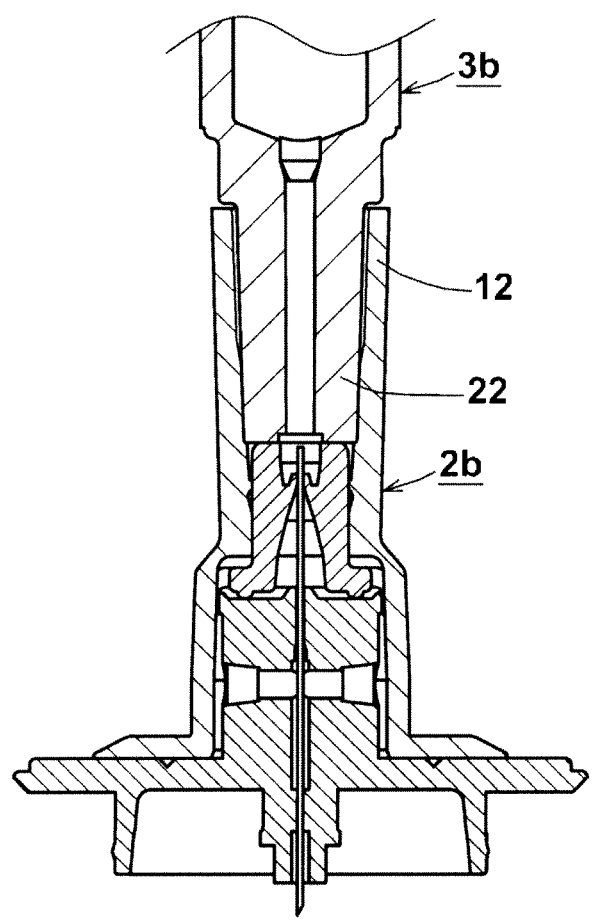
FIG. 9 is a partially enlarged sectional view illustrating an injection needle assembly and a drug injection device according to a third embodiment of the present invention.

FIG. 8 illustrates a second embodiment having another lock mechanism, and FIG. 9 illustrates a third embodiment having no lock mechanism.

A syringe 3a illustrated in FIG. 8 has a screw portion 24a serving as a lock mechanism at the back end on the outer periphery of a drug discharge tube 22. An injection needle assembly 2a has a screw portion 17a on the inner wall of a cylinder hole 12b of a fitting portion 12. In this example, the screw portion 24a is a male screw, while the screw portion 17a is a female screw. In the drug injection device 1a, the screw portions 17a and 24a are threadedly engaged with each other in the cylindrical hole 12b of the fitting portion 12.

The lock mechanism (screw portion) mounted to the drug discharge tube and the screw portion formed on the injection needle assembly are not limited to the above examples. It is only necessary that a male screw or a female screw corresponding to a lock mechanism is formed on a drug discharge tube, and a female screw or a male screw corresponding to the lock mechanism is formed on a fitting portion.

A drug discharge tube 22 of a syringe 3b illustrated in FIG. 9 does not have a lock mechanism 23 and an injection needle assembly 2b does not have a screw portion 17 on a fitting portion 12. In the drug injection device 1b, the drug discharge tube 22 and the injection needle assembly 2b are fitted to each other only by the fitting of the outer edge of the tip of the drug discharge tube 22 to a fitted wall 12c of the fitting portion 12.

As for the holding force for holding the injection needle assemblies 2, 2a, and 2b attached to the drug discharge tube 22, the injection needle assembly 2 and the drug injection device 1 illustrated in FIGS. 1 to 7 have the strongest holding force, the injection needle assembly 2a and the drug injection device 1a illustrated in FIG. 8 has the second strongest holding force, and the injection needle assembly 2b and the drug injection device 1b illustrated in FIG. 9 has the third strongest holding force. Any shape may be appropriately used for a lock mechanism, and whether a lock mechanism is provided or not may also be appropriately selected, according to a gauge or injection pressure of an injection needle.

The example in which N=6 in the taper ratio of the drug discharge tube 22 has been described. However, N can be changed as necessary. The value of M at the fitting portion 12 may be changed according to N. The taper ratio of the fitting portion 12 may be set as M=6, and the taper ratio of the drug discharge tube 22 may be set as M>N. The example in which the cylindrical hole 12b of the fitting portion 12 has the guide wall 12d has been described. However, the entire cylindrical hole 12b may be formed from the fitted wall 12c without having the guide wall 12d. The first member 14 and the second member 15 of the injection needle assembly 2 may be integrally formed with the same member. The injection needle assembly 2 may be configured to have a long projecting needle tip without having the adjustment portion 42 or the stabilization portion 44, for example. The example in which the drug discharge tube 22 is attached to the tip of the syringe 3 has been described. However, the drug discharge tube 22 may be attached to a tip of a tube through which a drug flows, for example.

EXAMPLES

Examples of the present invention will be described in detail below. However, the scope of the present invention is not limited to these examples.

Examples 1 to 4 illustrate manufacturing examples for experimentally producing injection needle assemblies to which the present invention is applied, and Comparative Examples 1 and 2 illustrate manufacturing examples for experimentally producing injection needle assemblies to which the present invention is not applied.

As Examples 1 to 4 and Comparative Example 1, injection needle assemblies illustrated in FIGS. 1 to 7 were prepared, each injection needle assembly having a different taper ratio of a fitted wall of a fitting portion. The injection needle assembly in Comparative Example 2 was prepared such that the entire fitting portion had a taper ratio of 6/100, which is a conventional product. Each of these injection needle assemblies was manufactured with a size corresponding to a drug discharge tube (diameter of a tip of a taper: 3.95 mm) with a taper ratio of 6/100. In Examples 1 to 4 and Comparative Examples 1 and 2, cycloolefin polymer (ZEONEX™, manufactured by Nippon Zeon Co., Ltd.) was used. Table 1 illustrates the taper ratios and sizes in Examples 1 to 4 and Comparative Examples 1 and 2.

TABLE 1

| Injection needle assembly | Taper ratio | Taper tip diameter Dmin (mm) | Note |
|---|---|---|---|
| Example 1 | 9/100 | 3.789 | |
| Example 2 | 12/100 | 3.723 | |
| Example 3 | 15/100 | 3.657 | |
| Example 4 | 18/100 | 3.591 | |
| Comparative Example 1 | 6/100 | 3.526 | |
| Comparative Example 2 | 6/100 | 4.260 | Conventional product |

Leakage Test

Test Method

A syringe having a drug discharge tube with a taper shape of 6/100 was prepared. The material used for the syringe was cycloolefin polymer (ZEONEX™, manufactured by Nippon Zeon Co., Ltd.). The needle tip of the injection needle in each of Examples 1 to 4 and Comparative Examples 1 and 2 was sealed with a hot melt adhesive resin, and the injection needle was attached to the drug discharge tube of the syringe. The syringe was filled with water colored with red and, using a load measuring device (AUTOGRAPH™ AGS-J-4, manufactured by Shimadzu Corporation), a pusher inserted into the syringe was pushed with a speed of 30 mm/min and a load when the water began to leak from the fitted portion (tapered shape portion) between the drug discharge tube and each of the injection needle assemblies was measured.

Test Results

Figure 10:
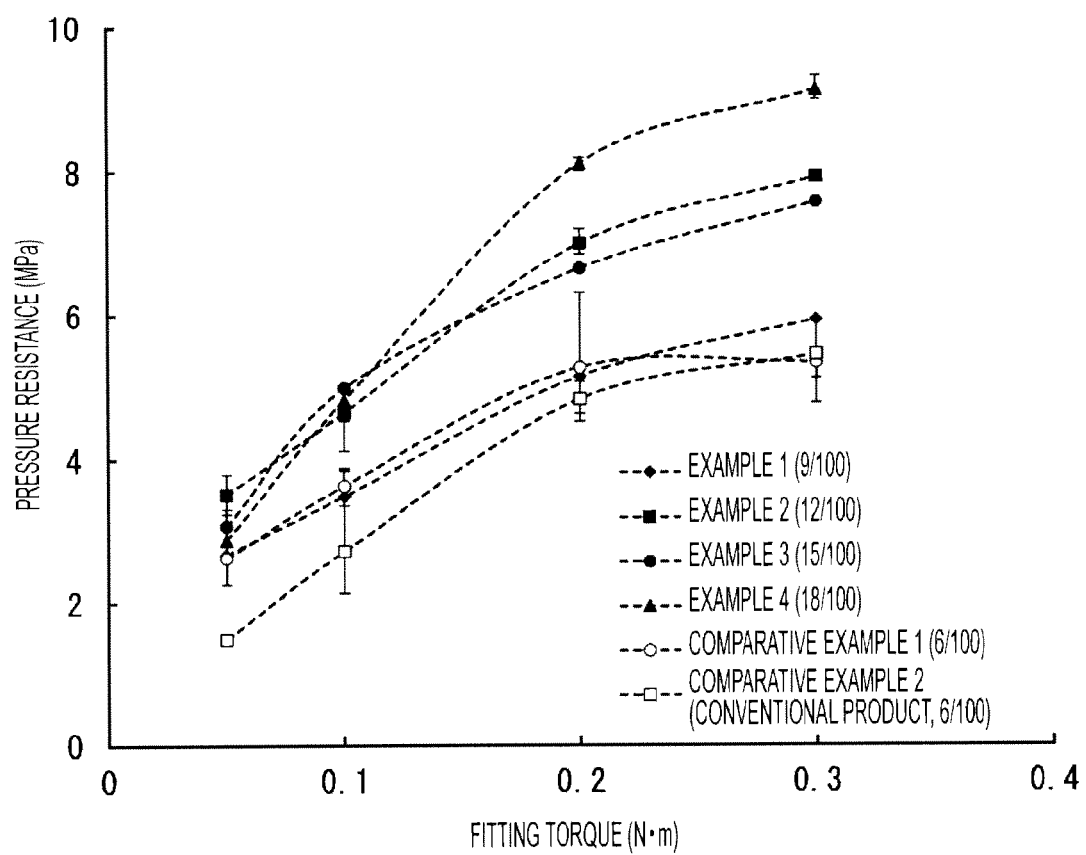
FIG. 10 is a graph illustrating results of a leakage test for Examples 1 to 4 and Comparative Examples 1 and 2.

FIG. 10 illustrates the test results. The injection needle assemblies in Examples 1 to 4 have a pressure resistance that is higher than the pressure resistance of the assembly in Comparative Example 2, which is a conventional product.

When the injection needle assembly is attached to the drug discharge tube with a weak force, a fitting torque becomes about 0.1 N·m. Pressure applied to the fitted portion upon injection becomes a maximum of 3 MPa, although the pressure varies depending on the type of injection. Therefore, if the pressure resistance is 3 MPa when the fitting torque is 0.1 N·m, the injection needle assembly can be used without causing leakage even if the injection needle assembly is attached with a weak force.

In each of Examples 1 to 4, pressure resistance was equal to or larger than 3 MPa when the fitting torque is 0.1 N·m. Especially in the second to fourth examples in which the taper ratio was 12/100 to 18/100, pressure resistance was equal to or larger than 4 MPa when the fitting torque was 0.1 N·m.

In Comparative Example 1, in which the taper ratio is 6/100, pressure resistance is equal to or larger than 3 MPa when the fitting torque is 0.1 N·m. This is considered as described below. Specifically, a fitted wall taper-fitted to the drug discharge tube and an extension wall not taper-fitted to the drug discharge tube are formed on the fitting portion such that a taper-fitted area becomes less than that in Comparative Example 2, which is the conventional product. Therefore, pressure is concentrated, whereby the injection needle assembly is closely taper-fitted than in the conventional product.

Insertion Distance Test

Figure 11:
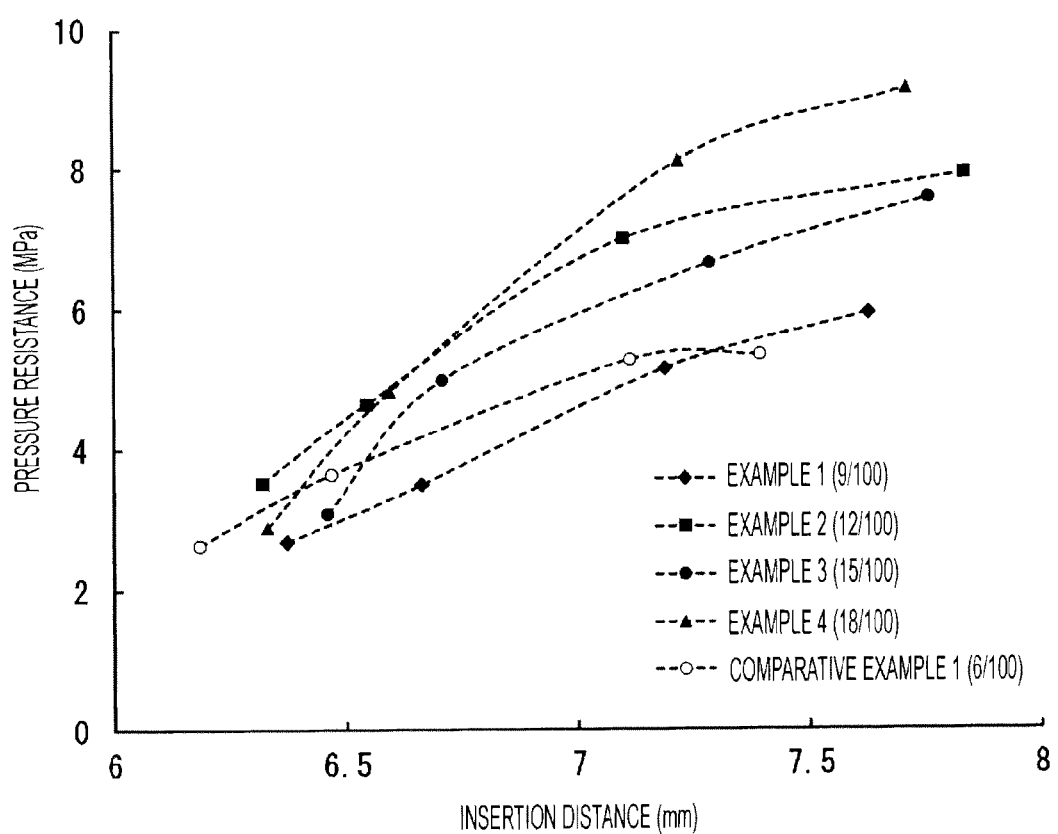
FIG. 11 is a graph illustrating results of an insertion distance test for Examples 1 to 4 and Comparative Example 1.

The relationship between a distance by which the drug discharge tube is inserted from the fitting opening of the injection needle assembly and pressure resistance was measured. The pressure resistance was measured in the same way as the leakage test. FIG. 11 illustrates the measurement results. In each example, pressure resistance increased as the insertion distance increased.

The injection needle assembly and the drug injection device according to certain embodiments of the present invention are used for administrating drug solution to a patient.

What is claimed is:

1. An injection needle assembly comprising:
an injection needle; and
a hub configured to hold the injection needle,
wherein the hub comprises a fitting portion comprising a fitting opening at one end, and an inner fitted wall having a female taper shape with an inner diameter that decreases in a direction from the fitting opening toward an inner side of the fitting portion;
wherein the fitting portion is configured to be fitted to a drug discharge tube comprising an outer wall having a male taper shape with an outer diameter that decreases in a direction toward a tip of the drug discharge tube; and
wherein, at least at a portion of the fitted wall at which an outer edge of the tip of the drug discharge tube contacts the fitted wall when the fitting portion is fitted to the drug discharge tube, a taper ratio of the female taper shape of the fitted wall is greater than a taper ratio of the male taper shape of the drug discharge tube.

2. The injection needle assembly according to claim 1, wherein the taper ratio of the female taper shape of the fitted wall is greater than 6/100.

3. The injection needle assembly according to claim 1, wherein the taper ratio of the female taper shape of the fitted wall is 1.5 to 10 times the taper ratio of the male taper shape of the outer wall of the drug discharge tube.

4. The injection needle assembly according to claim 1, wherein the fitting portion further comprises a guide wall located on a fitting opening side of the fitted wall, the guide wall having a diameter greater than a maximum diameter of the female taper shape of the fitted wall.

5. The injection needle assembly according to claim 1, wherein the fitting portion comprises a screw portion at an outer surface of the fitting portion, the screw portion of the fitting portion being configured to threadedly engage with a screw portion of a lock mechanism of the drug discharge tube.

6. A drug injection device comprising:
a syringe comprising the drug discharge tube recited in claim 1; and
the injection needle assembly according to claim 1.

7. An injection needle assembly comprising:
an injection needle; and
a hub configured to hold the injection needle, wherein the hub comprises a fitting portion comprising a fitting opening at one end, and an inner fitted wall having a female taper shape with an inner diameter that decreases in a direction from the fitting opening toward an inner side of the fitting portion;
wherein the fitting portion is configured to be fitted to a drug discharge tube comprising an outer wall having a male taper shape with an outer diameter that decreases in a direction toward a tip of the drug discharge tube; and
wherein, at least at a portion of the fitted wall at which an outer edge of the tip of the drug discharge tube contacts the fitted wall when the fitting portion is fitted to the drug discharge tube, a taper ratio of the female taper shape of the fitted wall is greater than 9/100.

8. The injection needle assembly according to claim 7, wherein a taper ratio of the female taper shape of the fitted wall is in a range of 9/100 to 60/100.

9. The injection needle assembly according to claim 7, wherein a taper ratio of the female taper shape of the fitted wall is in a range of 12/100 to 30/100.

10. The injection needle assembly according to claim 7, wherein a taper ratio of the female taper shape of the fitted wall is in a range of 12/100 to 18/100.

11. The injection needle assembly according to claim 7, wherein the fitting portion further comprises a guide wall located on a fitting opening side of the fitted wall, the guide wall having a diameter greater than a maximum diameter of the female taper shape of the fitted wall.

12. The injection needle assembly according to claim 7, wherein the fitting portion comprises a screw portion at an outer surface of the fitting portion.

13. A drug injection device comprising:
a syringe comprising the drug discharge tube recited in claim 7; and
the injection needle assembly according to claim 7.

14. The injection needle assembly according to claim 1, wherein a taper ratio of the female taper shape of the fitted wall is greater than 9/100.

15. The injection needle assembly according to claim 1, wherein a taper ratio of the female taper shape of the fitted wall is in a range of 9/100 to 60/100.

16. The injection needle assembly according to claim 1, wherein a taper ratio of the female taper shape of the fitted wall is in a range of 12/100 to 30/100.

17. The injection needle assembly according to claim 1, wherein a taper ratio of the female taper shape of the fitted wall is in a range of 12/100 to 18/100.

* * * * *